(12) United States Patent
Takada et al.

(10) Patent No.: US 11,399,708 B2
(45) Date of Patent: Aug. 2, 2022

(54) ENDOSCOPE ILLUMINATION UNIT AND ENDOSCOPE

(71) Applicant: OLYMPUS CORPORATION, Tokyo (JP)

(72) Inventors: Keisuke Takada, Kokubunji (JP); Hiromasa Okano, Tachikawa (JP); Kazuki Honda, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 173 days.

(21) Appl. No.: 16/787,654

(22) Filed: Feb. 11, 2020

(65) Prior Publication Data
US 2020/0170494 A1 Jun. 4, 2020

Related U.S. Application Data

(63) Continuation of application No. PCT/JP2018/029670, filed on Aug. 7, 2018.

(30) Foreign Application Priority Data

Aug. 23, 2017 (JP) .............................. JP2017-160000

(51) Int. Cl.
*A61B 1/07* (2006.01)
*A61B 1/00* (2006.01)
(Continued)

(52) U.S. Cl.
CPC ............ *A61B 1/07* (2013.01); *A61B 1/00096* (2013.01); *A61B 1/0607* (2013.01);
(Continued)

(58) Field of Classification Search
CPC ............ A61B 1/00009; A61B 1/00045; A61B 1/0008; A61B 1/00096; A61B 1/00165;
(Continued)

(56) References Cited

U.S. PATENT DOCUMENTS

2013/0137923 A1* 5/2013 Honda ............... A61B 1/00096
600/109
2014/0347878 A1* 11/2014 Honda ............... A61B 1/00177
362/574
(Continued)

FOREIGN PATENT DOCUMENTS

CN 103313644 A 9/2013
CN 104203070 A 12/2014
(Continued)

OTHER PUBLICATIONS

International Search Report dated Oct. 30, 2018 issued in PCT/JP2018/029670.

*Primary Examiner* — Michael J Carey
*Assistant Examiner* — Julianna J Nicolaus
(74) *Attorney, Agent, or Firm* — Scully, Scott, Murphy & Presser, P.C.

(57) ABSTRACT

An endoscope illumination unit includes: an incident part into which illuminating light guided via a light guide enters; a light guide body that includes an annular section having an inner peripheral surface and that guides the illuminating light having entered via the incident part and emits the illuminating light from an outer surface of the annular section; and a reflective sheet that has opposite end portions and that is provided on the inner peripheral surface of the annular section and scatters the illuminating light, having entered the light guide body, within the annular section. The opposite end portions of the reflective sheet bent in conformity to the inner peripheral surface of the annular section is positioned at a portion of the inner peripheral surface remote from the incident part.

20 Claims, 12 Drawing Sheets

(51) Int. Cl.
*A61B 1/06* (2006.01)
*F21V 8/00* (2006.01)

(52) U.S. Cl.
CPC .......... *A61B 1/0669* (2013.01); *G02B 6/0045* (2013.01); *G02B 6/0051* (2013.01); *A61B 1/00009* (2013.01); *A61B 1/00045* (2013.01)

(58) Field of Classification Search
CPC ....... A61B 1/05; A61B 1/0607; A61B 1/0623; A61B 1/0669; A61B 1/07; G02B 6/0045; G02B 6/0051; G02B 6/0055; G02B 23/2469; G02B 23/2484; G02B 23/26
See application file for complete search history.

(56) References Cited

U.S. PATENT DOCUMENTS

| | | | |
|---|---|---|---|
| 2016/0103312 A1* | 4/2016 | Furuta | A61B 1/00096 362/558 |
| 2016/0106306 A1* | 4/2016 | Furuta | A61B 1/0623 600/176 |
| 2017/0269348 A1 | 9/2017 | Shinji | |

FOREIGN PATENT DOCUMENTS

| | | | |
|---|---|---|---|
| EP | 2 649 923 A1 | 10/2013 | |
| EP | 2815691 A1 | 12/2014 | |
| JP | 2012-125411 A | 7/2012 | |
| JP | 2013-125735 A | 6/2013 | |
| WO | WO2014/073426 A1 | 5/2014 | |
| WO | WO2016/088267 A1 | 6/2016 | |
| WO | WO-2016098203 A1 * | 6/2016 | ......... A61B 1/00096 |

\* cited by examiner

ENDOSCOPE ILLUMINATION UNIT AND ENDOSCOPE

CROSS REFERENCE TO RELATED APPLICATION

This application is a continuation application of PCT/JP2018/029670 filed on Aug. 7, 2018 and claims benefit of Japanese Application No. 2017-160000 filed in Japan on Aug. 23, 2017, the entire contents of which are incorporated herein by this reference.

BACKGROUND OF THE INVENTION

1. Field of the Invention

The present invention relates to an endoscope illumination unit and an endoscope.

2. Description of the Related Art

Endoscopes have heretofore been used widely in medical and industrial fields. By inserting an elongated insertion section of an endoscope into a subject, a user, such as an endoscope operator, can observe the inside of the subject.

An illumination unit provided with an illuminating optical system is provided on a distal end section of the insertion section to irradiate illuminating light to the subject. Light reflected from the subject enters an observation window provided on the distal end section of the insertion section. The light having entered the observation window is radiated to a light receiving surface of an image pickup device, and the image pickup device photoelectrically converts an image of the subject formed on the light receiving surface to thereby output an image pickup signal.

Generally, the illuminating optical system includes a plurality of lenses in a case where the illuminating optical system has to provide illumination in an inserting direction of the insertion section along an axis direction of the insertion section. In addition to the aforementioned type, another type of endoscope has also been proposed which is provided with an illuminating optical system including an annular section, as disclosed for example in International Publication No. WO2014/073426.

Specifically, International Publication No. WO2014/073426 discloses an illuminating optical system that includes a reflective member for diffusing light, guided into the annular section, to emit the light in a predetermined direction. The reflective member is formed by coating aluminum or the like, having a high reflectivity with respect to illuminating light, in a thin film state.

SUMMARY OF THE INVENTION

An endoscope illumination unit according to an aspect of the present invention is an endoscope illumination unit provided on a distal end section of an insertion section of an endoscope, including: an incident part into which illuminating light guided via a light guide from an external light source enters; a transparent light guide body including an annular section or a partly annular section having an inner peripheral surface, the light guide body guiding the illuminating light having entered from the incident part and also emitting the illuminating light from an outer surface of the annular section or the partly annular section; and a scattering section provided on the inner peripheral surface of the annular section or the partly annular section, the scattering section scattering the illuminating light, having entered the light guide body, within the annular section or the partly annular section, the scattering section being formed by bending a sheet, having opposite end portions, in conformity to the inner peripheral surface, wherein the sheet is wound in conformity to the inner peripheral surface of the annular section or the partly annular section in such a manner that the opposite end portions of the sheet approach each other to be positioned at a portion of the inner peripheral surface remote from the incident part.

An endoscope according to an aspect of the present invention includes an endoscope illumination unit according to an aspect of the present invention.

DETAILED DESCRIPTION OF THE PREFERRED EMBODIMENTS

Embodiments of the present invention will be described hereinafter with reference to the accompanying drawings.

Note that, in figures used in the following description, a dimensional scale is differentiated as appropriate for each component in order to enable the component element to be shown in a size readily recognizable in each of the figures, and that the present invention is not limited only to quantities, shapes, and size ratios of the component elements and to relative positional relationships among the component elements shown in the figures.

First Embodiment (Configuration of Endoscope Apparatus)

Figure 1:
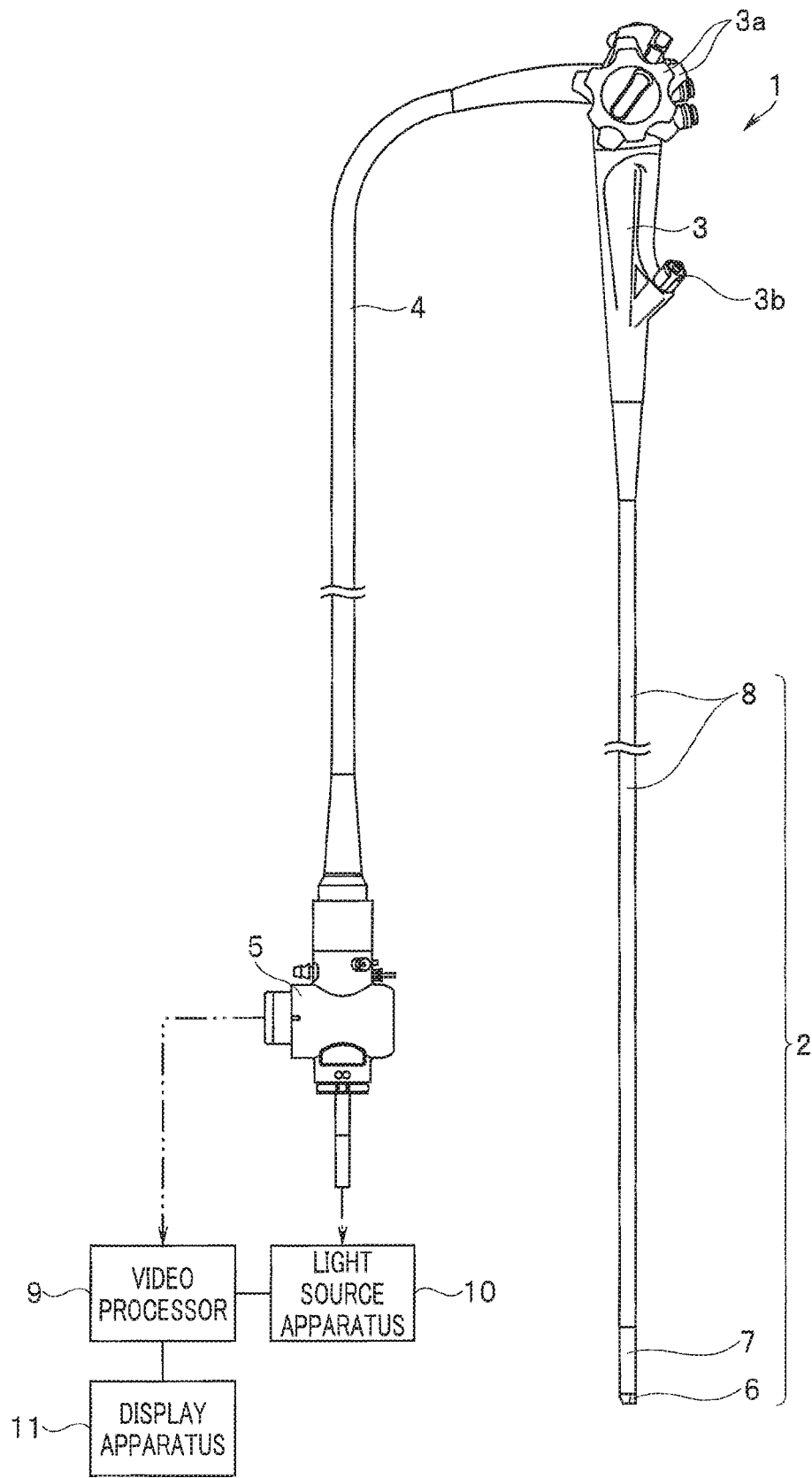
FIG. 1 is a schematic configuration view showing an overall configuration of an endoscope apparatus according to a first embodiment of the present invention.

FIG. 1 is a schematic configuration view showing an overall configuration of endoscope apparatus according to the first embodiment of the present invention.

As shown in FIG. 1, an endoscope 1 mainly includes, among other things: an elongated insertion section 2 to be inserted into a body cavity or the like; an operation section 3 connected to a proximal end side of the insertion section 2; a universal cord 4 extending from the operation section 3; and a connector section 5 provided on a distal end portion of the universal cord 4. The endoscope 1 also includes an endoscope illumination unit that will be described later.

The insertion section 2 includes a rigid distal end section 6 provided on a most distal end area of the insertion section 2, a bending portion 7 connected to a proximal end side of the distal end section 6, and a flexible tubular portion 8 constituted by an elongated tubular member having flexibility and connected to a proximal end side of the bending portion 7.

A video processor 9 and a light source apparatus 10 are connected to the connector section 5, and a display apparatus 11 is connected to the video processor 9. An endoscope system is constituted by the endoscope 1, the video processor 9, the light source apparatus 10, and the display apparatus 11.

The operation section 3 is a part to be grasped by a user, who is a doctor or the like, when using the endoscope 1, and bending operation knobs 3a and a plurality of other operation members corresponding to various other operations are disposed on an outer surface of the operation section 3. Each of the bending operation knobs 3a is an operation member that, in response to the user pivotally operating the knob 3a with his or her finger or the like, enables the bending portion 7 of the insertion section 2 to bend in any desired one of up-and-down and left-and-right directions.

A treatment instrument insertion port 3b for insertion of a treatment instrument (not shown) is formed in a part of the operation section 3 close to a distal end of the operation section 3 and near a connection part connecting with the insertion section 2. The treatment instrument insertion port 3b is in communication with a treatment instrument channel (not shown) inserted into the interior of the insertion section 2.

The video processor 9 not only comprehensively controls the entire endoscope system, but also performs predetermined image processing on an image pickup signal acquired in the endoscope 1 to thereby generate an endoscope image. The display apparatus 11 is a display section that displays the endoscope image based on an image signal of the endoscope image supplied from the video processor 9, and an LCD panel or the like is applied as the display apparatus 11.

The light source apparatus 10 contains, among other things, a lamp, such as a xenon lamp or a halogen lamp, or a light emitting diode to generate illuminating light. Respective proximal end portions of a plurality of light guides inserted in the endoscope 1 are disposed in the light source apparatus 10, and light from the lamp or the like enters the respective proximal end portions of the light guides. Respective distal end portions of the light guides are disposed within the distal end section 6 of the insertion section 2. Thus, the light having entered the proximal end portion of each of the light guides is emitted from the distal end portion of the light guide.

(Configuration of Distal End Section 6 of Insertion Section 2)

Figure 2:
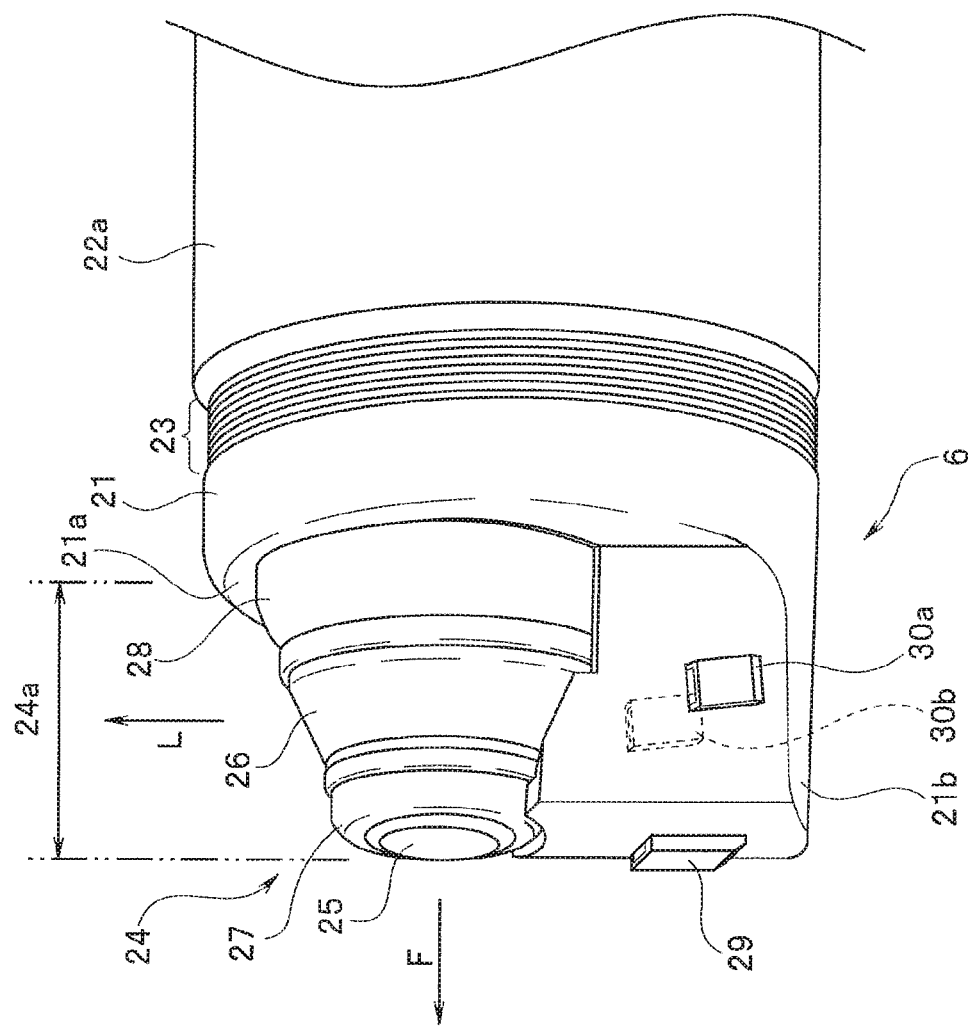
FIG. 2 is a perspective view showing, at an enlarged scale, a distal end section 6 of an insertion section 2 of an endoscope 1 according to the first embodiment of the present invention.
Figure 3:
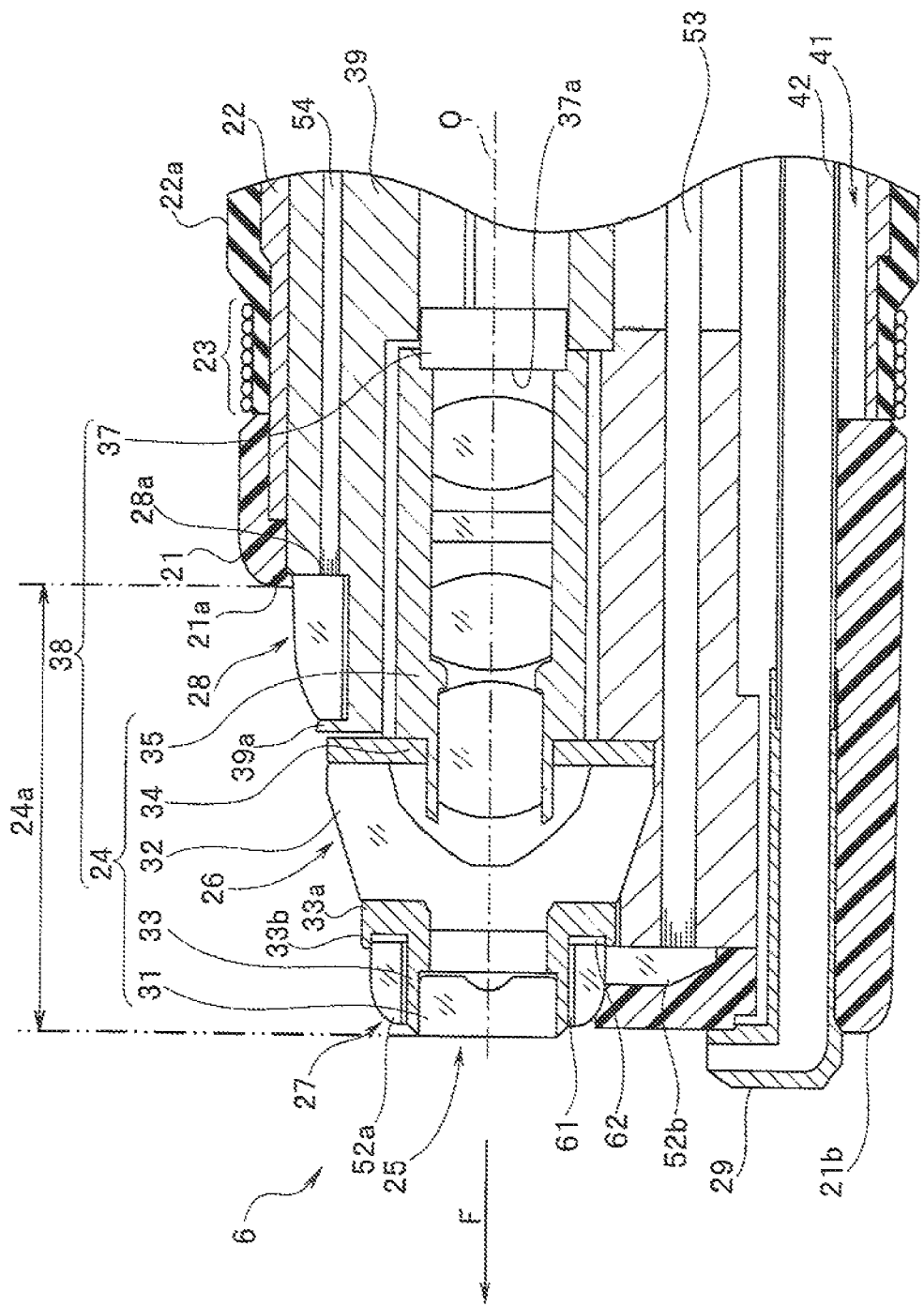
FIG. 3 is a sectional view of the distal end section 6 of the insertion section 2 taken along a center axis of the insertion section 2 according to the first embodiment of the present invention.

FIG. 2 is a perspective view showing, at an enlarged scale, the distal end section 6 of the insertion section 2 of the endoscope 1, and FIG. 3 is a sectional view of the distal end section 6 of the insertion section 2 taken along a center axis of the insertion section 2.

The distal end section 6 of the insertion section 2 includes a distal end section body 21 formed of a resin. A blade 22 and a rubber sheath member 22a cover the insertion section 2. A distal end portion of the sheath member 22a is fixed to the distal end section body 21 by a bobbin member 23. The bobbin member 23 is coated with an adhesive.

A lens unit 24 is provided on the distal end section 6 and includes an image picking-up optical system of the endoscope 1. The lens unit 24 (FIG. 3) is disposed in such a manner that its distal end side portion 24a of the lens unit 24 protrudes from a distal end surface 21a of the distal end section body 21.

A circular front observation window 25, which is a first observation window for observing a front side F in an inserting direction of the insertion section 2 along the axis direction of the insertion section 2, is provided on the distal end side portion 24a of the lens unit 24. In other words, the distal end side portion 24a of the lens unit 24 is a protruding portion that protrudes from the distal end surface 21a of the distal end section 6 along a longitudinal axis direction of the insertion section 2, and the front observation window 25 is a window provided on the distal end side portion 24a for observing an area located on the front side F in the inserting direction.

A side observation window 26, which is a second observation window having a partly annular shape (namely, in this case, a shape at least including part of a circular ring with opposite ends spaced from each other), is provided closer to the proximal end of the lens unit 24 than the front observation window 25. Namely, the side observation window 26 is provided on a peripheral side surface of the lens unit 24 in a circular shape along a circumferential periphery direction of the lens unit 24, and the side observation window 26 is located rearward of the front observation window 25 in the longitudinal axis direction of the insertion section 2. The side observation window 26 has a tapered outer surface such that an outer diameter of the side observation window 26 decreases gradually in the inserting direction of the insertion section 2. The side observation window 26 is a window provided on the distal end side portion 24a for observing a side area located laterally outward, namely in an outer diameter direction, of the window 26.

The front observation window 25 acquires a first subject image of a first area of a subject into which the insertion section 2 is inserted, and the side observation window 26 acquires a second subject image of a second area of the subject which differs at least in part from the first area. The first subject image acquired by the front observation window 25 is a subject image of the first area located on the front side F of the insertion section 2 along the longitudinal axis direction of the insertion section 2, and the second subject image acquired by the side observation window 26 is a subject image of the second area located on a lateral side L of the insertion section 2, namely laterally outward of the insertion section 2 in a direction intersecting the longitudinal axis. Therefore, the endoscope 1 is a wide-field-of-view-type endoscope capable of simultaneously observing both a front field and a side field.

The distal end section body 21 includes a protruding portion 21b that protrudes toward the front side F from the distal end surface 21a. The protruding portion 21b is provided adjacent to the distal end side portion 24a and protrudes from the distal end surface 21a of the distal end section 6 along the longitudinal axis of the insertion section 2. The protruding portion 21b is shaped to cover part of a side surface of the distal end side portion 24a of the lens unit 24.

A first illumination section 27 is provided between the front observation window 25 and the side observation window 26, and a second illumination section 28 is provided between the side observation window 26 and the distal end surface 21a.

The first illumination section 27 has an annular shape such that the illumination section 27 surrounds a periphery of the circular front observation window 25. The first illumination section 27 emits illuminating light mainly toward the front side F, and also emits illuminating light toward the lateral side L from an outer peripheral surface of the illumination section 27.

The second illumination section 28 has a partly annular shape and emits illuminating light mainly toward the lateral side L. The second illumination section 28 is disposed to emit illuminating light in an observing direction of the side observation window 26.

The protruding portion 21b of the distal end section body 21 is a distal end structure of a substantially rectangular parallelepiped shape in which a distal end surface of the protruding portion 21b has a substantially same height (substantially the same protruding height toward the front side F) as the front observation window 25. Three cleaning nozzles 29, 30a, and 30b are provided on the protruding portion 21b. The cleaning nozzle 29, which is for cleaning a surface of the front observation window 25, is disposed on a distal end surface of the protruding portion 21b near the front observation window 25. The cleaning nozzle 29 blows out a cleaning liquid toward the front observation window 25 in a direction parallel to the distal end surface of the protruding portion 21b.

The other two cleaning nozzles 30a and 30b, which are for cleaning a surface of the side observation window 26, are disposed on two opposite side surface positions of the protruding portion 21b. The two cleaning nozzles 30a and 30b are provided near two ends of the side observation window 26 having a partly annular shape for blowing out a cleaning liquid toward the surface of the side observation window 26.

Note that an opening portion (not shown) of a treatment instrument insertion hole for insertion of forceps or the like is also provided in the distal end section body 21.

As shown in FIG. 3, the lens unit 24 includes the image picking-up optical system provided with a plurality of lenses including a front observing lens 31 and a side observing lens 32. The front observing lens 31 has a circular column shape, and the side observing lens 32 has a substantially truncated cone shape. The side observation window 26 is part of a slant surface portion of the lens of the substantially truncated cone shape.

The lens unit 24 also includes frame members 33, 34, and 35 arranged sequentially in a direction from the distal end section 6 of the insertion section 2 toward the proximal end of the distal end section 6. Each of the frame members 33, 34, and 35 has a cylindrical shape.

A frame member 33 located closest to the distal end of the distal end section 6 has an outward flange portion 33a at a proximal end of the frame member 33. The front observing lens 31 and another optical member are fixed within the frame member 33 by an adhesive or the like, and a distal end surface of the front observing lens 31 constitutes the front observation window 25. A light blocking portion 33b is provided on an outer peripheral portion of the outward flange portion 33a for blocking light, emitted from the first illumination section 27, from entering the side observation window 26.

The frame member 34 has an annular shape. The side observing lens 32 is fixed by an adhesive or the like in such a manner that the side observing lens 32 is sandwiched between the outward flange portion 33a of the frame member 33 and the frame member 34.

A distal end portion of the frame member 35 is inserted and fixed in a hole of the frame member 34 by an adhesive or the like. Optical members, such as a plurality of lenses, constituting the image picking-up optical system are fixed within the frame member 35 by an adhesive or the like. The frame member 36 is fixed to the frame member 35 by an adhesive or the like.

An image pickup device 37 is fixed to a proximal end side of the lens unit 24. The image pickup device 37 has a light receiving surface 37a that receives light from the lens unit 24, and the light receiving surface 35a is fixed to the frame member 36 by an adhesive or the like in such a manner that the light receiving surface 37a perpendicularly intersects an optical axis O of the image picking-up optical system of the lens unit 24 and the optical axis O passes through the center of the light receiving surface 37a.

The lens unit 24 and the image pickup device 37 together constitute an image pickup unit 38. The image pickup unit 38 is fixed within the distal end section body 21 by a fixing member 39.

A distal end portion of the fixing member 39 has a partly annular portion protruding radially outward and the partly annular portion constitutes a light blocking portion 39a that blocks light, emitted from the second illumination section 28, from entering the side observation window 26.

Three channels for three water delivering tubes for the three cleaning nozzles 29, 30a, and 30b are formed within the distal end section body 21. A channel 41 of such three channels is shown in FIG. 3, and the water delivering tube 42 for the cleaning nozzle 29 is inserted in the channel 41 within the distal end section body 21. A distal end of the water delivering tube 42 is inserted in and fixed to a proximal end portion of the cleaning nozzle 29 by an adhesive or the like.

(Configuration of Illumination Unit)

Next, a description will be given of the illumination unit that constitutes the first illumination section 27.

Figure 4:
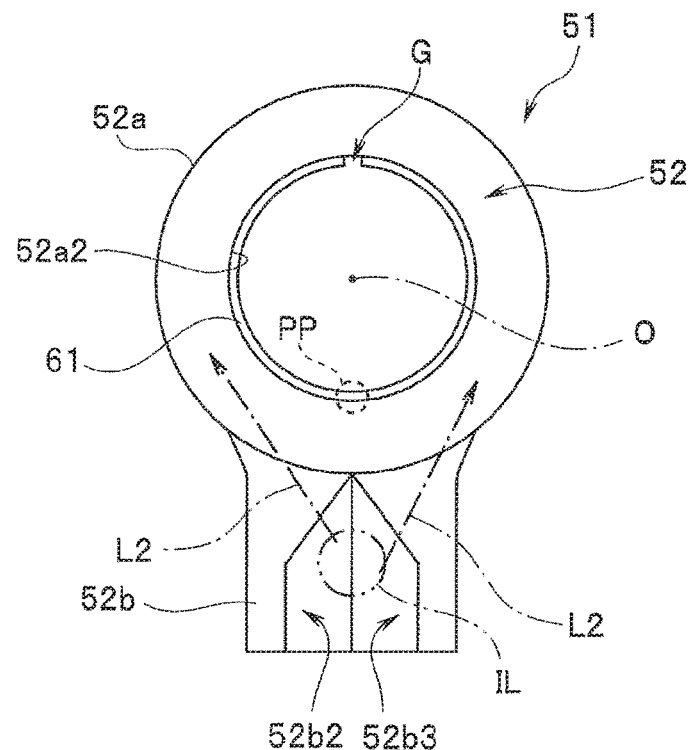
FIG. 4 is a front view of an illumination unit 51 according to the first embodiment of the present invention.
Figure 5:
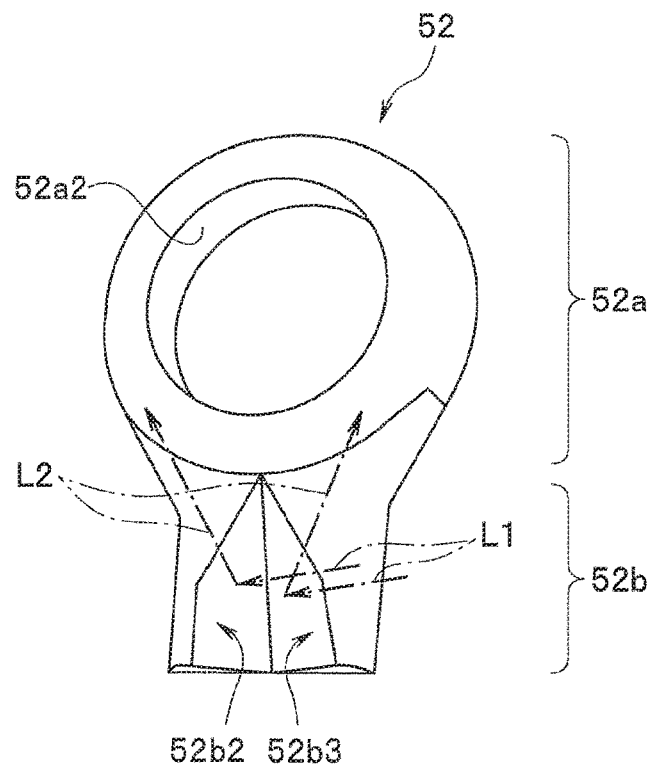
FIG. 5 is a perspective view of a light guide body 52 of the illumination unit 51 as viewed from a front side according to the first embodiment of the present invention.
Figure 6:
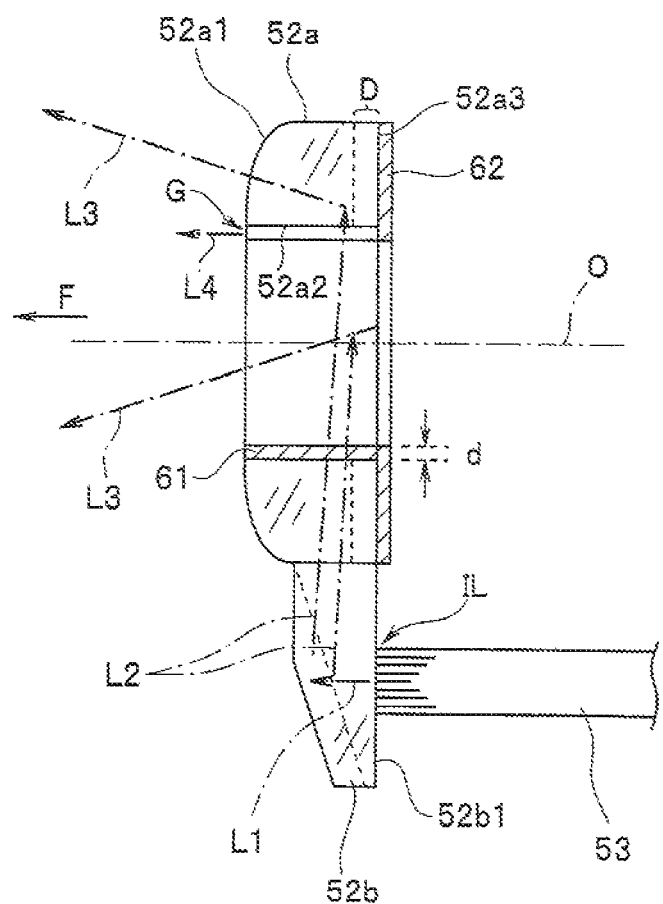
FIG. 6 is a sectional view of the illumination unit 51 taken along an optical axis O according to the first embodiment of the present invention.

FIGS. 4 to 6 show only the endoscope illumination unit provided in the distal end portion of the endoscope 1. FIG. 4 is a front view of the illumination unit 51; that is, FIG. 4 shows the illumination unit 51 as viewed from a front side of the endoscope. FIG. 5 is a perspective view of a light guide body 52 of the illumination unit 51 as viewed from the front side, and FIG. 6 is a sectional view of the illumination unit 51 taken along the optical axis O direction.

The illumination unit 51 includes the light guide body 52. The light guide body 52 is an optical device that includes an annular section 52a and a protruding section 52b that protrudes radially outward from the annular section 52a. A surface of the protruding section 52b is coated with aluminum; note, however, that an area of the outer surface of the protruding section 52b which a light guide 53 contacts is not coated with aluminum. The light guide body 52 is a transparent member in which the annular section 52a and the protruding section 52b are formed integrally with each other. The light guide body 52 is formed of glass or resin, and particles of a light scattering material, such as titanium oxide, are scattered within a proximal end side portion of the annular section 52a. A range D depicted by dotted lines in FIG. 6 shows a light scattering layer in which fine particles of the aforementioned titanium oxide are scattered.

As will be described later, light emitted from the light source apparatus 10 is guided to the distal end section 6 via the light guide inserted in the endoscope 1. Light emitted from the distal end surface of the light guide enters an incident part IL of the protruding section 52b, is guided into the annular section 52a of the light guide body 52, and is then emitted from the outer surface of the annular section 52a.

As shown in FIG. 6, the annular section 52a is an annular optical section processed and formed in such a manner that a front outer peripheral portion of the annular section 52a has a curved surface portion 52a1 as viewed in section. As shown in FIGS. 2 and 3, the annular section 52a is disposed to surround an outer peripheral portion of the front observing lens 31 and adjacent to a distal end of the side observation window 26. The annular section 52a has such an optical directivity as to emit illuminating light mainly toward the front side F which is the inserting direction of the insertion section 2.

As shown in FIG. 4, a reflective sheet 61 is attached to an inner peripheral surface 52a2 of the annular section 52a by a transparent adhesive.

The reflective sheet 61, which is of a type called a high reflection sheet, is a band-shaped, multi layer that has been subjected to reflection processing. The reflective sheet 61 has been also subjected to processing to uniformly scatter light on an outer surface of the reflective sheet 61. A thickness d of the reflective sheet 61 is, for example, about 0.7 mm, and a reflectivity of the reflective sheet 61 is, for example, about 98% or over. The surface of the reflective sheet 61 constitutes a scattering section that scatters and reflects incident light.

The band-shaped reflective sheet 61 has such a length that a gap G is formed between opposite end portions of the reflective sheet 61 when the reflective sheet 61 is attached to the inner peripheral surface 52a2 of the annular section 52a in close contact with each other. Namely, a length in a longitudinal direction of the band-shaped reflective sheet 61 is smaller than a length in a peripheral direction of the inner peripheral surface 52a2 of the annular section 52a. A width in a transverse direction of the reflective sheet 61 is equal to a thickness along the optical axis O direction of the annular section 52a. The band-shaped reflective sheet 61 is attached by an adhesive or the like to the inner peripheral surface 52a2 of the annular section 52a in close contact with each other.

Further, the reflective sheet 61 is attached to the inner peripheral surface 52a2 of the annular section 52a in such a manner that the gap G is located at a portion remotest from the incident part IL via which light enters the annular section 52a. The incident part IL is located within the protruding portion 21b. Illuminating light guided via the light guide 53 from the light source apparatus 10, which is an external light source, enters the incident part IL.

Furthermore, an annular reflective sheet 62 is attached by an adhesive or the like to a rear-side back surface 52a3 of the annular section 52a facing in a direction opposite from the inserting direction of the insertion section 2. The reflective sheet 62 is the same sheet as the reflective sheet 61. The reflective sheet 62 has an annular shape having a width equal to a width of the annular section 52a.

As set forth above, the light guide body 52, which is a transparent member, includes the annular section 52a having the inner peripheral surface 52a2, and the light guide body 52 not only guides illuminating light having entered via the incident part IL but also emits the illuminating light via the outer surface of the annular section 52a.

Further, the scattering section is provided on the inner peripheral surface 52a2 of the annular section 52a outside the front observation window 25 in such a manner as to surround the front observation window 25. The reflective sheet 61, having the opposite end portions, scatters within the light guide body 52 the illuminating light having entered the light guide body 52, is formed by being curved in conformity to the inner peripheral surface 52a2.

Furthermore, the reflective sheet 61, which is attached to the inner peripheral surface 52a2 of the annular section 52a in close contact with the inner peripheral surface 52a2 in such a manner that the opposite end portions of the reflective sheet 61 are located at a portion of the inner peripheral surface 52a2 remotest from the incident part IL when the reflective sheet 61 is attached to the inner peripheral surface 52a2. Thus, the gap G between the opposite end portions of the reflective sheet 61 is located at a portion remotest from the incident part IL, as shown in FIG. 4. In other words, a central portion of the reflective sheet 61 is located closest to the incident part IL.

A flat light incident surface 52b1 is formed on the rear-side back surface of the protruding section 52b. The incident part IL is a portion of the light incident surface 52b1. The light incident surface 52b1 is formed in a plane parallel to a plane perpendicularly intersecting the longitudinal direction of the insertion section 2, and the distal end section of the light guide 53 extending from the light source apparatus 10 is positioned and fixed within the protruding portion 21b in such a manner that the distal end surface of the light guide 53 contacts the light incident surface 52b1.

Two reflecting surfaces 52b2 and 52b3 are formed on a front side of the protruding section 52b by the front side of the protruding section 52b being cut in a substantially V-groove shape.

The protruding section 52b constitutes a light deflecting section that receives via the light incident surface 52b1 light emitted from the light guide 53, reflects the received light by the two reflecting surfaces 52*b*2 and 52*b*3 to thereby deflect the light, and guides the deflected light toward the annular section 52*a*.

The light guided from the protruding section 52*b* into the annular section 52*a* is scattered or reflected within the annular section 52*a* and emitted mainly forward from the outer surface of the annular section 52*a*. Namely, the light guide body 52 is provided in the distal end side portion 24*a* protruding from the distal end surface 21*a* of the distal end section 6 along the longitudinal axis direction of the insertion section 2, and illuminating light is emitted toward the front side F in the inserting direction of the insertion section 2 and laterally in the outer diameter direction of the annular section 52*a*.

Further, as shown in FIG. 3, the second illumination section 28, which has a partly annular shape, is also composed of a light guide body that is a transparent optical member and that has a flat light incident surface 28*a* formed on a rear-side back surface of the light guide body. The light incident surface 28*a* is formed parallel to a plane perpendicularly intersecting the longitudinal direction of the insertion section 2, and the distal end surface of the light guide 54 extending from the light source apparatus 10 is fixed within the distal end section 6 in such a manner that the distal end surface of the light guide 54 contacts the light incident surface 28*a*.

Light emitted from the light guide 54 is guided into the second illumination section 28, scattered or reflected within the second illumination section 28, and then emitted from an outer surface of the second illumination section 28 toward the lateral side L in the outer diameter direction.

The light guide body of the second illumination section 28 is also formed of glass or resin and may have a scattering layer within which particles of a scattering material, such as titanium oxide, are scattered.

The light guide body of the second illumination section 28 is also provided in the distal end side portion 24*a* protruding from the distal end surface 21*a* of the distal end section 6 along the longitudinal axis direction of the insertion section 2.

(Operation)

Light enters the light guide body 52 of the illumination unit via the incident part IL of the light incident surface 52*b*1. The light having entered the light guide body 52 is reflected by the two reflecting surfaces 52*b*2 and 52*b*3 but also guided into the annular section 52*a* while being scattered or reflected within the light guide body 52.

The light within the annular section 52*a* is reflected by the reflective sheets 61 and 62 and emitted mainly toward the front side F from the outer surface of the annular section 52*a*.

More specifically, the light emitted from the distal end surface of the light guide 53 enters the incident part IL of the protruding section 52*b*. The light having entered the incident part IL travels within the protruding section 52*b* as depicted by arrow L1 in FIGS. 5 and 6. The light having entered the incident part IL is not only reflected by the two reflecting surfaces 52*b*2 and 52*b*3 but also guided into the annular section 52*a* as depicted by arrow L2 in FIGS. 4 to 6 while being scattered or reflected within the light guide body 52.

The light is reflected by the reflective sheets 61 and 62 within the annular section 52*a* and then emitted mainly forward from the outer surface of the annular section 52*a* as depicted by arrow L3 in FIG. 6.

The light also leaks out through the gap G because the gap G is located at a portion remotest from the incident part IL of the light guide body 52; namely, in the light having entered the incident part IL, light of a light quantity having decreased most leaks out. Thus, illumination unevenness formed on the illuminated subject by the light leaking out through the gap G is the smallest, with the result that good illumination efficiency of the illuminating light is achieved.

Figure 7:
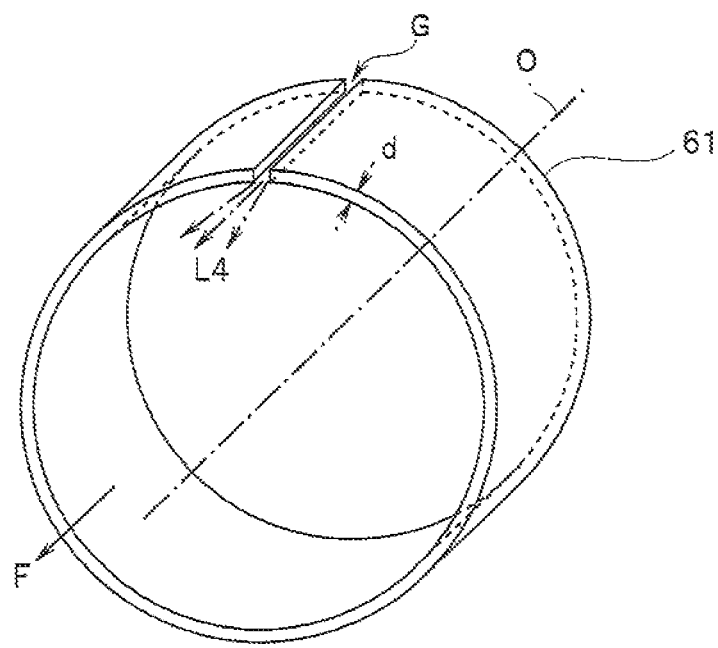
FIG. 7 is a perspective view of a reflective sheet 61 attached to an inner peripheral surface of an annular section 52a according to the first embodiment of the present invention.

FIG. 7 is a perspective view of the reflective sheet 61 attached to the inner peripheral surface of the annular section 52*a*. Light from the annular section 52*a* not shown in FIG. 7 leaks out toward the front side F through the gap G between the opposite end portions of the reflective sheet 61 as depicted by arrow L4 in FIG. 7.

Figure 8:
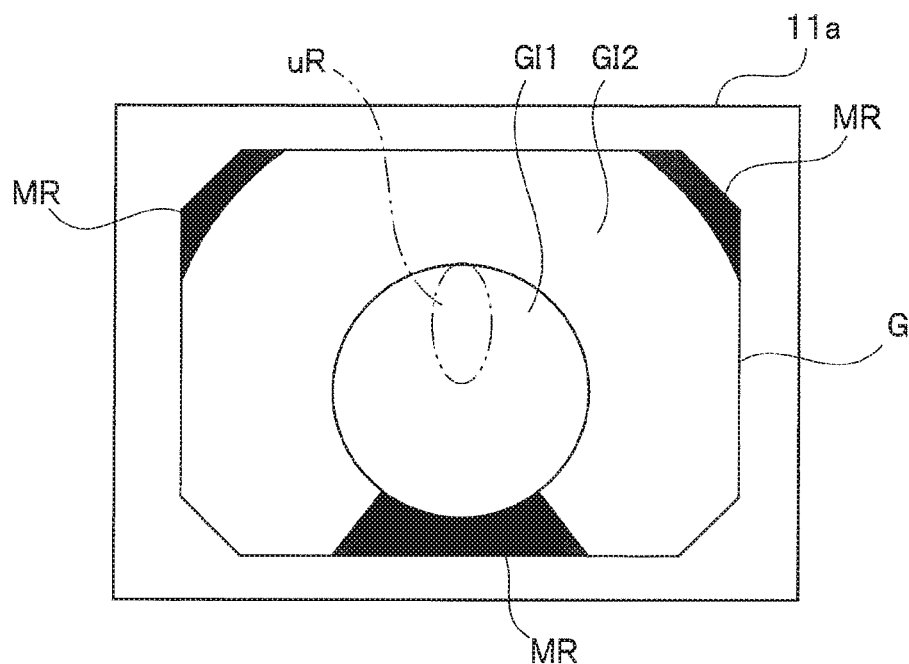
FIG. 8 is a view explaining an example of an endoscope image when a gap G is located at a portion remotest from an incident part IL of the light guide body 52 according to the first embodiment of the present invention.
Figure 9:
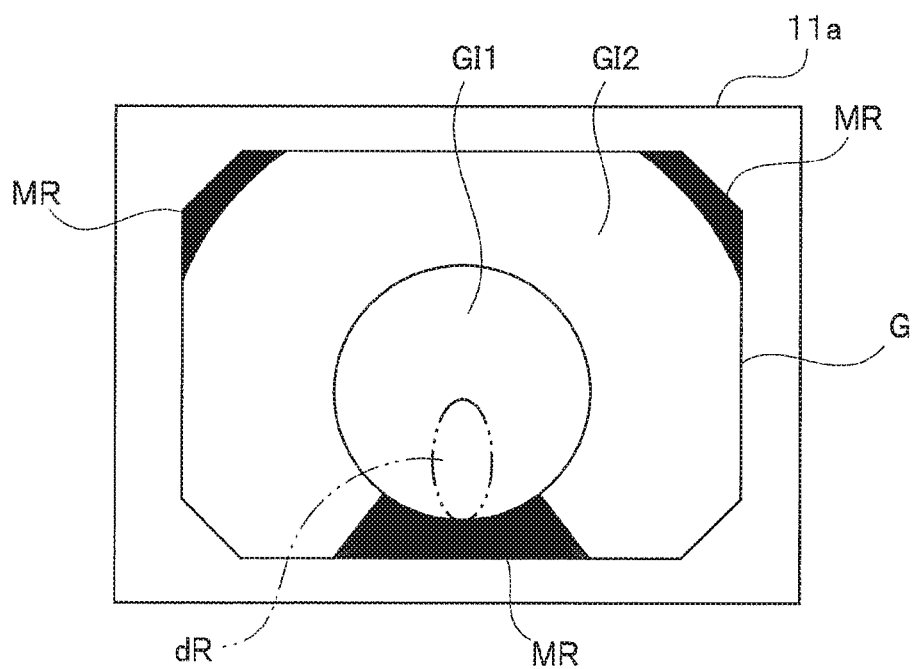
FIG. 9 is a view explaining an example of an endoscope image when the gap G is located at a portion near the incident part IL of the light guide body 52 (for example, at a position depicted by PP in FIG. 4) according to the first embodiment of the present invention.

FIGS. 8 and 9 are views explaining displayed examples of endoscope images. FIG. 8 is a view illustrating an example of an endoscope image when the gap G is located at a portion remotest from the incident part IL of the light guide body 52 as shown in FIGS. 4 to 6. FIG. 9 is a view illustrating an example of an endoscope image when the gap G is located at a portion near the incident part IL of the light guide body 52 (for example, at a position depicted by PP in FIG. 4).

FIGS. 8 and 9 show the endoscope images G displayed on a display screen 11*a* of the display apparatus 11. The endoscope images G each include a front image G11 and a side image G12. The front image G11 has a circular shape, and the side image G12 has a partly annular shape surrounding the front image G11. The endoscope images G each also include a plurality of (three in this case) mask regions MR where no image is displayed.

If the gap G is located at the position PP near the incident part IL of the annular section 52*a* (see FIG. 4), light of a large light quantity in the light having entered the incident part IL leaks out through the gap G. Thus, large illumination unevenness is formed on the illuminated subject by the light leaking out through the gap G, which results in decreased illumination efficiency of the illuminating light.

In such a case, there occurs illumination unevenness in which a lower area dR is brighter than the other areas as shown in FIG. 9.

By contrast, if the gap G is located at a portion remotest from the incident part IL of the annular section 52*a* as shown in FIG. 4, light leaking out through the gap G, if any, has a light quantity having decreased most in the light having entered the incident part IL, so illumination unevenness formed on the illuminated subject by the light leaking out through the gap G is smaller than the illumination unevenness shown in FIG. 9.

Thus, degree of illumination unevenness in which an upper area uR is brighter than the other areas can be decreased as shown in FIG. 8.

With the present embodiment, as can be seen from the foregoing description, it is possible to provide an endoscope illumination unit and an endoscope which can suppress illumination unevenness of illuminating light by an illuminating optical system including an annular part and can suppress a decrease of illumination efficiency of the illuminating light.

Note that although the reflective sheet 61 is attached to the inner peripheral surface of the annular section 52*a* in such a manner that the gap G is located at a portion remotest from the incident part IL of the annular section 52*a* in the above-described embodiment, the gap G may be located at any other position within the annular section 52*a* as remote as possible from the incident part IL.

Figure 10:
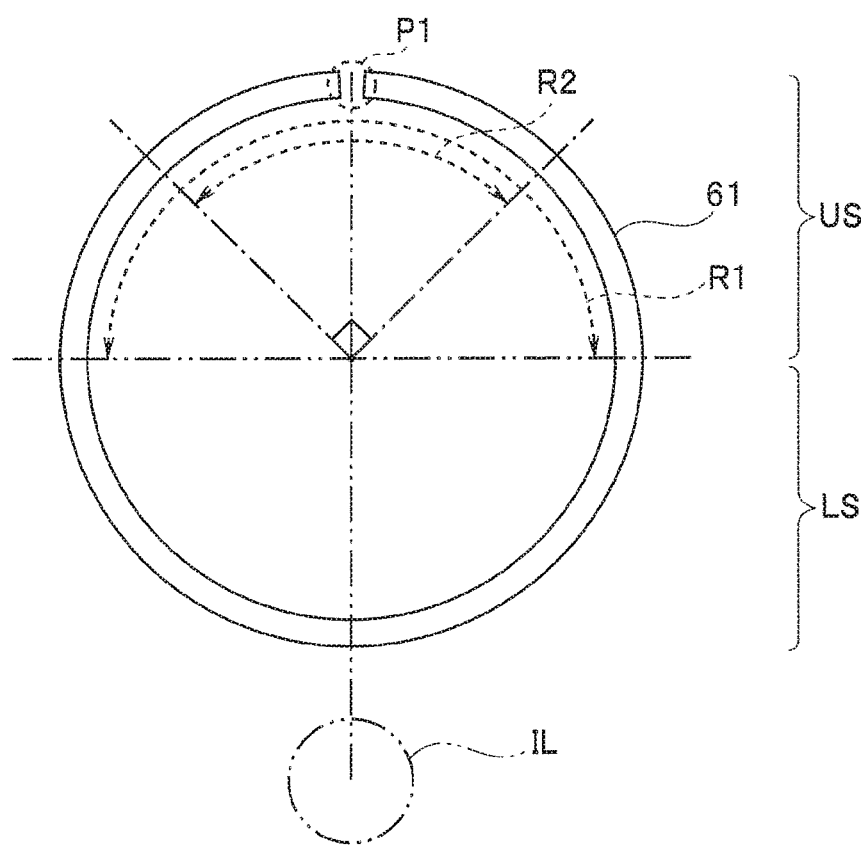
FIG. 10 is a view explaining a position of the gap G when the distal end section 6 is viewed from the front side F according to the first embodiment of the present invention.

FIG. 10 is a view explaining a position of the gap G when the distal end section 6 is viewed from the front side F. In the above-described embodiment, the reflective sheet 61 is attached to the inner peripheral surface of the annular section 52*a* in such a manner that the opposite end portions of the reflective sheet 61 are located at a portion P1 remotest from the incident part IL of the light guide body 52 (in the example of FIG. 10, at the portion including a point remote by 180° from the incident part IL with respect to the optical axis O) when the distal end section 6 is viewed from the front side F. The opposite end portions of the substantially circular reflective sheet 61 are located at the portion P1 in an upper area of FIG. 10.

Alternatively, the reflective sheet 61 may be attached to the inner peripheral surface of the annular section 52*a* in such a manner that the opposite end portions of the reflective sheet 61 are located at positions remote from the incident part IL of the light guide body 52 within a half angular range R1 of the inner peripheral surface 52*a*2 of the annular section 52*a*. In the example of FIG. 10, the opposite end portions of the substantially circular reflective sheet 61 only has to be located within an upper half region about the optical axis O. Namely, the opposite end portions of the reflective sheet 61 only has to be located within the angular range R1 of 180° opposite from the incident part IL with respect to the optical axis O (namely within a range remote by 90° or over from the incident part IL with respect to the optical axis O).

If the opposite end portions of the reflective sheet 61 are located within a lower half region LS (namely a half region closer to the incident part IL) in FIG. 10, illumination unevenness increases because the light quantity in the lower half region LS is larger than in the upper half region US. However, if the opposite end portions of the reflective sheet 61 are located in the upper half region US in FIG. 10, illumination unevenness decreases because the light quantity in the upper half region US decreases as compared to the light quantity in the lower half region LS.

Further, note that it is preferable that the opposite end portions of the substantially circular reflective sheet 61 are located within a range of 90° in the upper half region US of FIG. 10 as depicted by R2. Specifically, it is more preferable that the opposite end portions of the reflective sheet 61 are located within a range of 45° leftward and rightward about the optical axis O from the portion P1 remotest from the incident part IL of the light guide body 52.

If the opposite end portions of the reflective sheet 61 are located within a range R2 of 90° of the upper half region US in FIG. 10, illumination unevenness decreases because the light quantity decreases as compared to the light quantity within a range of 45° to 90° leftward and rightward about the optical axis O from the portion P1 remotest from the incident part IL of the light guide body 52.

As noted above, the gap G between the opposite end portions of the reflective sheet 61 may be located at any portion of the inner peripheral surface 52*a*2 remote from the incident part IL other than the portion of the inner peripheral surface 52*a*2 remotest from the incident part IL.

Second Embodiment

In the above-described first embodiment, the light guide body 52 includes the protruding section 52*b* that guides light to the annular section 52*a*, and the distal end surface of the light guide 53 is attached to the protruding section 52*b* in close contact with the protruding section 52*b*. By contract, in the second embodiment, the distal end surface of the light guide 53 is attached directly to the annular section 52*a*.

An endoscope system according to the second embodiment has the same configuration as the endoscope system according to the first embodiment as shown in FIG. 1. The distal end section 6 of the insertion section 2 in the second embodiment has the same contour as the distal end section 6 in the first embodiment as shown in FIG. 2.

Although an inner configuration of the distal end section 6 of the insertion section 2 in the second embodiment is substantially the same as the inner configuration of the distal end section 6 in the first embodiment shown in FIG. 3, a configuration of the light guide body of the illumination unit in the second embodiment differs from the configuration of the light guide body 52 in the first embodiment.

A light guide body 52A of an illumination unit 51A in the second embodiment includes only the annular section 52*a* of the light guide body 52 in the first embodiment. The distal end surface of the light guide 53 is attached directly to the back surface of the light guide body 52A.

In the following description of the second embodiment, only components differing from the components provided in the first embodiment will be described, and same components as in the first embodiment are depicted with same reference characters as used for the first embodiment and will not be described.

Figure 11:
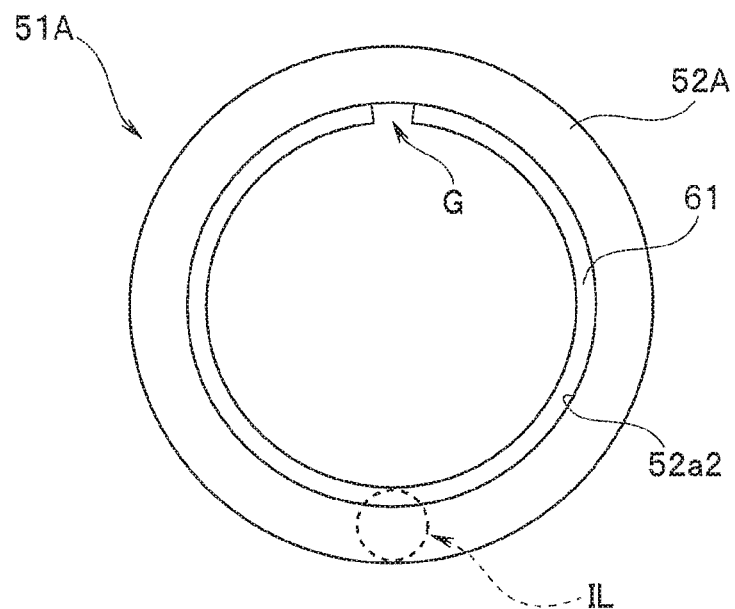
FIG. 11 is a front view of an illumination unit 51A according to a second embodiment of the present invention.

FIG. 11 is a front view of the illumination unit 51A provided in the second embodiment and shows the illumination unit 51A as viewed from the front side of the endoscope.

As shown in FIG. 11, the illumination unit 51A includes the light guide body 52A having an annular shape and the reflective sheet 61 attached by an adhesive or the like to the inner peripheral surface 52*a*2 of the light guide body 52A.

As noted above, the light guide body 52A is the same as the annular section. 52*a* provided in the first embodiment and has such an optical directivity as to emit illuminating light mainly toward the front side F which is the inserting direction of the insertion section 2.

The rear-side back surface of the light guide body 52A opposite the front side of the light guide body 52A has a flat surface, and the distal end surface of the light guide 53 is attached directly to the flat surface. A region of the back surface of the light guide body 52A to which the distal end surface of the light guide 53 is attached directly is the incident part IL.

In the second embodiment, the reflective sheet 61 is also attached to the inner peripheral surface 52*a*2 of the light guide body 52A in such a manner that the gap G between the opposite end portions of the reflective sheet 61 is located at a portion remotest from the light incident part IL, as shown in FIG. 11.

Thus, with the second embodiment, it is also possible to provide an endoscope illumination unit and an endoscope which can suppress illumination unevenness of illuminating light by an illuminating optical system including an annular part and can suppress a decrease of illumination efficiency of the illuminating light.

Note that in a case where light enters the light guide body 52A via a plurality of light guides, a plurality of reflective sheets 61 may be attached to the inner peripheral surface 52*a*2 of the light guide body 52A in such a manner that a plurality of gaps G are formed and that each of the gaps G is located at a portion remotest from a corresponding incident part IL.

Figure 12:
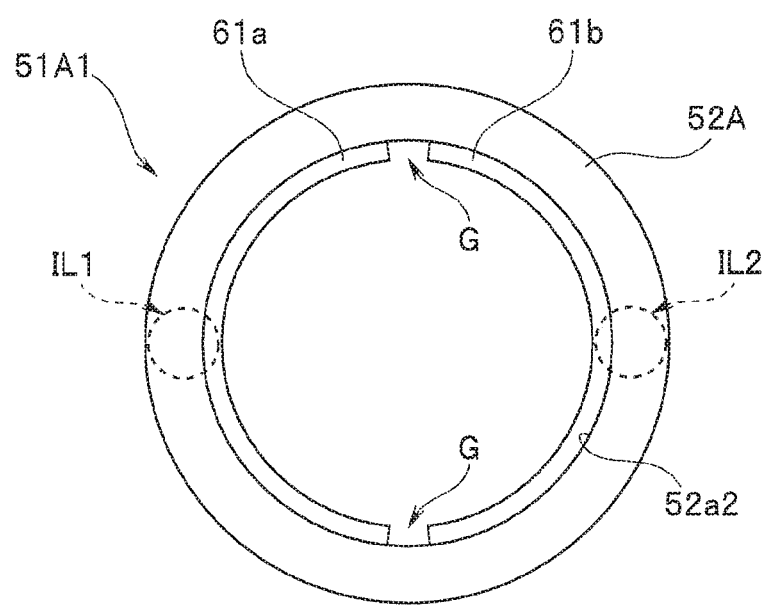
FIG. 12 is a front view of an illumination unit 51A1 including a plurality of reflective sheets according to the second embodiment of the present invention.

FIG. 12 is a front view of an illumination unit 51A1 including a plurality of reflective sheets according to the second embodiment. FIG. 12 shows the illumination unit 51A1 as viewed from the front side F of the endoscope.

As shown in FIG. 12, respective distal end surfaces of two light guides are attached directly to the light guide body 52A, and the light guide body 52A includes two incident parts IL1 and IL2. Two reflective sheets 61a and 61b are attached to the inner peripheral surface 52a2 of the light guide body 52A.

The two incident parts IL1 and IL2 are located at positions remotest from each other about the optical axis O, for example, remote from each other by about 180°.

Two gaps G are formed between the two reflective sheets 61a and 61b, and the reflective sheets 61a and 61b are attached to the inner peripheral surface 52a2 of the light guide body 52A in such a manner that each of the gaps G is located at a portion remotest from the two incident parts IL1 and IL2. The two gaps G are located at positions remote from each other by 180° about the optical axis O.

Opposite end portions of the reflective sheet 61a are located remotest from the incident part IL1, and opposite end portions of the reflective sheet 61b are located remotest from the incident part IL1. In other words, a central portion of the reflective sheet 61a is located closest to the incident part IL1, and a central portion of the reflective sheet 61b is located closest to the incident part IL2.

With the configuration of FIG. 12, it is also possible to achieve effects similar to the aforementioned effects achieved by the second embodiment.

Further, note that although the light guide body 52A in FIG. 12 has an annular shape, the light guide body may be composed of a plurality of light guide bodies each having a partly annular shape.

Figure 13:
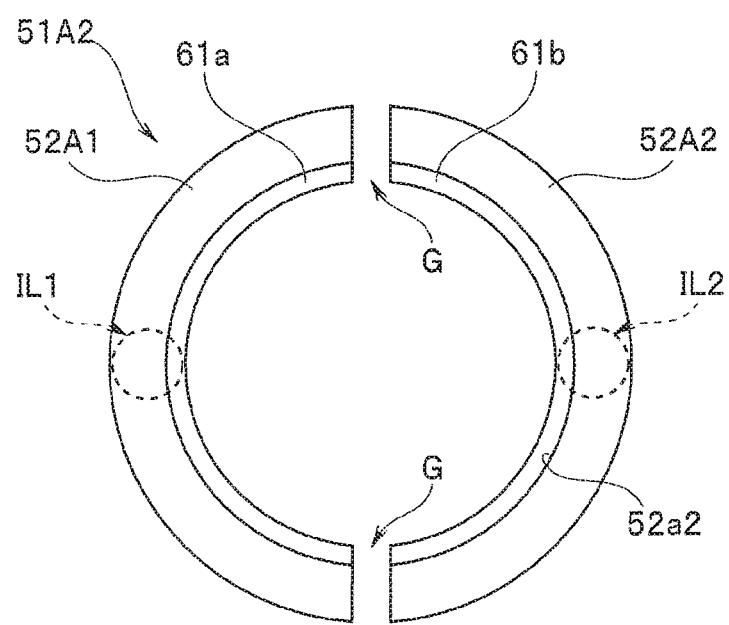
FIG. 13 is a front view of an illumination unit 51A2 including a plurality of partly annular light guide bodies according to the second embodiment of the present invention.

FIG. 13 is a front view of an illumination unit 51A2 including a plurality of light guide bodies each having a partly annular shape according to the second embodiment. FIG. 13 shows the illumination unit 51A2 as viewed from the front side F of the endoscope.

In FIG. 13, the illumination unit 51A2 includes two light guide bodies 52A1 and 52A2, and each of the two incident parts IL1 and IL2 are located at a central portion of a corresponding one of the light guide bodies 52A1 and 52A2 each having a partly annular shape. Each of the gaps G is located at a portion remotest from the two incident parts IL1 and IL2.

With the configuration of FIG. 13, it is also possible to achieve effects similar to the aforementioned effects achieved by the configuration of FIG. 12.

Next, a description will be given of modifications of the above-described two embodiments.

Modification 1

Although the gap G is formed in a direction perpendicularly intersecting the optical axis O in each of the above-described embodiments, the gap U may be formed at a predetermined angle to the direction perpendicularly intersecting the optical axis O.

Figure 14:
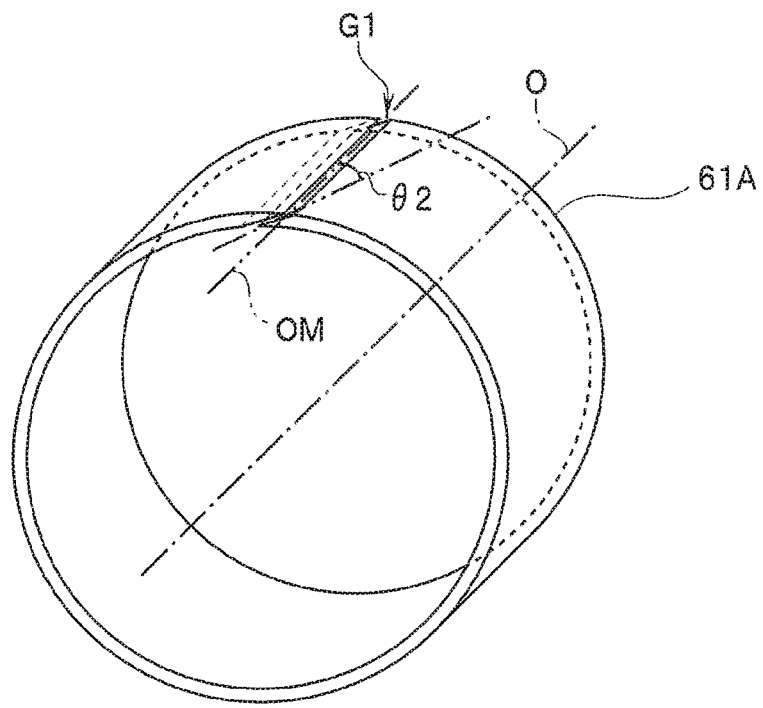
FIG. 14 is a perspective view of a reflective sheet 61A showing a gap G1 according to modification 1.
Figure 15:
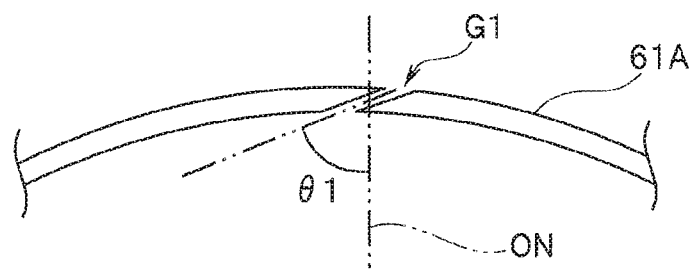
FIG. 15 is a partial front view of the reflective sheet 61A particularly showing the gap G1 according to modification 1.

FIG. 14 is a perspective view of a reflective sheet 61A showing a gap G1 according to a modification 1, and FIG. 15 is a partial front view of the reflective sheet 61A particularly showing the gap G1 according to the modification 1.

As shown in FIGS. 14 and 15, the gap G1 is formed at an angle θ1 to a direction ON toward the optical axis O and perpendicularly intersecting the optical axis O from a given point of the gap G.

Note that the gap G1 may be formed at an angle θ2 to a line OM parallel to the optical axis O as shown in FIG. 14.

With such modification 1, it is also possible to achieve effects similar to the effects achieved by the illumination units provided in the above-described two embodiments.

Modification 2

Although the gap G is not covered with anything in each of the above-described embodiments and the modification 1, a reflective member covering the gap G may be provided.

Figure 16:
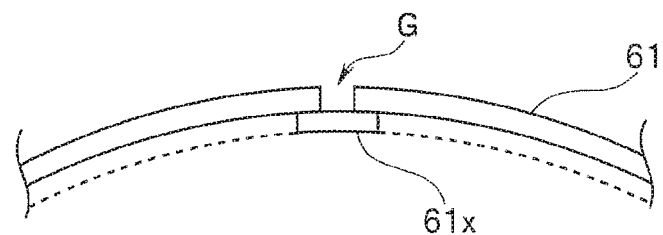
FIG. 16 is a partial front view of a reflective sheet 61 having a reflective member 61x covering the gap G according to modification 2.

FIG. 16 is a partial front view of the reflective sheet 61 having a reflective member 61x covering the gap G according to a modification 2.

As shown in FIG. 16, the reflective member 61x that is a same member as the reflective sheet 61 is attached by an adhesive or the like in such a manner as to cover the gap G of the reflective sheet 61 provided on the inner peripheral surface 52a2 of the annular section 52a of the light guide body 52 or the light guide body 52A.

With the reflective member 61x, it is possible to decrease a quantity of light leaking out toward the observation window in the light leaking outward the front side F through the gap G.

Note that although the reflective member 61x in FIG. 16 is a piece of sheet covering only the range of the gap G, another reflective sheet may be further attached in such a manner as to cover substantial entirety of the inner peripheral surface 52a2 of the annular section 52a including the range of the gap G of the reflective sheet 61. Namely, at least a part of the reflective sheet 61 may be formed in two layers.

With such modification 2, it is also possible to achieve effects similar to the effects achieved by the illumination units provided in the above-described two embodiments.

Modification 3

Although the reflective member 61x for covering the gap G is attached to the reflective sheet 61 in the above-described modification 2, the reflective sheet 61 may be attached to the inner peripheral surface 52a2 of the annular section 52a of the light guide body 52 or the light guide body 52A with the opposite end portions of the reflective sheet 61 superposed on each other.

Figure 17:
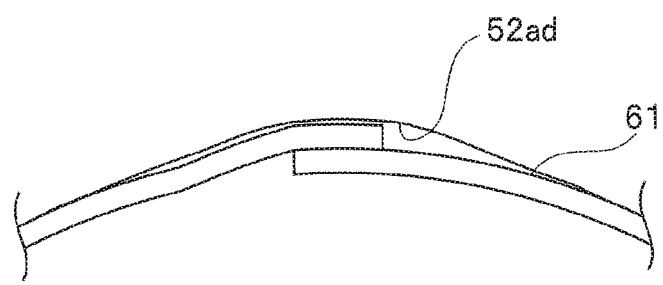
FIG. 17 is a partial front view of a reflective sheet 61 with opposite end portions of the sheet superposed on each other according to modification 3.

FIG. 17 is a partial front view of the reflective sheet 61 with the opposite end portions of the reflective sheet 61 superposed on each other according to a modification 3.

As shown in FIG. 17, the reflective sheet 61 is provided on the inner peripheral surface 52a2 of the annular section 52a of the light guide body 52 with the opposite end portions of the reflective sheet 61 superposed on each other. Illumination unevenness is likely to be formed by light, emitted from the superposed opposite end portions, being reflected by opposed reflective sheets.

Because a thickness of the superposed portions is two times a thickness d of the single reflective sheet 61, a hollow portion 52ad is formed on the inner peripheral surface of the annular section 52a.

The formation of the hollow portion 52ad can prevent an increase of a contour tolerance of the frame member 33 holding the front observing lens 31.

Note that the reflective sheet may be formed to have a corrugated sectional shape and such a corrugated reflective sheet may be attached to the inner peripheral surface 52a2 of the annular section 52a of the light guide body 52 or the light guide body 52A with the opposite end portions of the corrugated reflective sheet superposed on each other.

Figure 18:
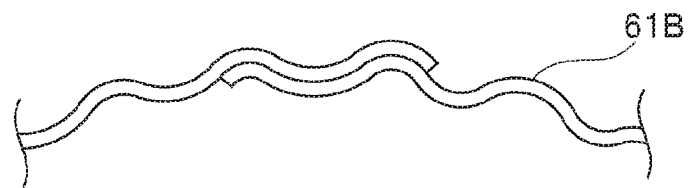
FIG. 18 is a partial front view of a reflective sheet 61B having a corrugated sectional shape with opposite end portions of the sheet superposed on each other according to another example of modification 3.

FIG. 18 is a partial front view of a reflective sheet 61B having a corrugated sectional shape with the opposite end portions superposed on each other according to another example of the modification 3.

As shown in FIG. 18, the reflective sheet 61B is provided on the inner peripheral surface 52a2 of the annular section 52a of the light guide body 52 with the opposite end portions of the reflective sheet 61B superposed on each other.

With such modification 3, it is also possible to achieve effects similar to the effects achieved by the illumination units provided in the above-described two embodiments.

According to the above-described two embodiments and various modifications, it is possible to provide an endoscope illumination unit and an endoscope which can suppress illumination unevenness of illuminating light by an illuminating optical system including an annular part and can also suppress a decrease of illumination efficiency of the illuminating light.

Note that while the illumination unit in each of the above-described embodiments and modifications has been described above as being applied as the illumination unit of the first illumination section 27 for forward illumination, such an illumination unit is also applicable to the second illumination section 28 for lateral illumination that is a partly annular section.

Namely, in the case where the aforementioned reflective sheet is provided on the inner peripheral surface of the light guide body of the second illumination section 28 that is a partly annular section for illuminating an area located laterally of the distal end section 6, the configuration of each of the above-described embodiments and modifications is also applicable.

The present invention is not limited to the above-described embodiments, and various modifications, alterations, etc. of the present invention are possible within a range where the gist of the present invention is not changed.

What is claimed is:

1. An endoscope illumination unit for use on a distal end section of an insertion section of an endoscope, the endoscope illumination unit comprising:
   an incident part having an incident surface onto which illuminating light guided via a light guide from an external light source enters the incident part;
   a transparent light guide body including an annular section formed at least partially in a circumferential direction, the annular section having an inner peripheral surface, the light guide body guiding the illuminating light having entered via the incident surface and emitting the illuminating light from an outer surface of the annular section; and
   a scattering material disposed on the inner peripheral surface of the annular section, the scattering material being configured to scatter the illuminating light, having entered the light guide body, within the annular section, the scattering material being a sheet having opposite ends, the opposite ends being applied to a continuous cylindrical portion of the inner peripheral surface of the annular section, wherein
   the sheet conforms to the inner peripheral surface of the annular section such that the opposite ends of the sheet are adjacent to each other and are positioned at the continuous cylindrical portion of the inner peripheral surface remote from the incident surface.

2. The endoscope illumination unit according to claim 1, wherein the sheet bent in conformity to the inner peripheral surface has a gap formed between the opposite ends to expose the continuous cylindrical portion of the inner peripheral surface, and the scattering material is provided on the inner peripheral surface such that the gap is located at the continuous cylindrical portion of the inner peripheral surface remote from the incident surface.

3. The endoscope illumination unit according to claim 2, wherein the gap is formed such that light leaks out through the gap in a distal direction.

4. The endoscope illumination unit according to claim 1, wherein the opposite ends of the sheet are positioned at the continuous cylindrical portion of the inner peripheral surface furthest from the incident surface.

5. The endoscope illumination unit according to claim 1, wherein the scattering material is configured to scatter light uniformly on a surface of the sheet.

6. The endoscope illumination unit according to claim 1, wherein the light guide body is provided on a first protruding portion that protrudes from a distal end surface of the distal end section along a longitudinal axis direction of the insertion section, and
   the illuminating light is emitted in a distal direction, and in a radial direction from the annular section.

7. The endoscope illumination unit according to claim 1, wherein:
   the inner peripheral surface is a circumferential surface having a first half covering 180° of the circumferential surface and a second half covering another 180° of the circumferential surface;
   the incident surface being positioned closest to a radial center of the first half of the circumferential surface; and
   the opposite ends of the sheet are positioned to correspond to the second half of the circumferential surface.

8. An endoscope comprising:
   the endoscope illumination unit according to claim 1; and
   the insertion section;
   wherein the endoscope illumination unit is disposed in the distal end section of the insertion section.

9. The endoscope according to claim 8, wherein the light guide body is provided on a first protruding portion that protrudes from a distal end surface of the distal end section along a longitudinal axis direction of the insertion section, and
   the illuminating light is emitted in a distal direction and in a radial direction of the annular section.

10. The endoscope according to claim 9, comprising an observation window provided on the first protruding portion for observing an area located distally from the observation window.

11. The endoscope according to claim 10, wherein the scattering material is provided outside the observation window to surround the observation window.

12. The endoscope according to claim 8, wherein the light guide body is provided on a first protruding portion that protrudes from a distal end surface of the distal end section along a longitudinal axis direction of the insertion section, and
   the illuminating light is emitted laterally in an outer diametric direction from the annular section.

13. The endoscope according to claim 12, further comprising an observation window provided on the first protruding portion for observing an area located laterally in the outer diametric direction.

14. The endoscope according to claim 8, wherein the light guide body is provided on a first protruding portion that protrudes from a distal end surface of the distal end section along a longitudinal axis direction of the insertion section, and
   the illuminating light is emitted distally and radially from the annular section,
   the endoscope including:

a first observation window provided on the first protruding portion for observing an area located distally from the first observation window; and a second observation window provided on the first protruding portion for observing an area located radially from the second observation window, wherein the second observation window is disposed proximally relative to the first observation window.

15. The endoscope according to claim 9, comprising a second protruding portion provided, adjacent to the first protruding portion, on the distal end section of the insertion section, the second protruding portion protruding from the distal end surface of the distal end section along the longitudinal axis direction of the insertion section, a distal end portion of the light guide being located within the second protruding portion.

16. The endoscope according to claim 15, wherein the incident surface is located within the second protruding portion.

17. The endoscope illumination unit according to claim 2, further comprising an other scattering material applied to cover the gap.

18. The endoscope illumination unit according to claim 1, wherein the opposite ends overlap circumferentially in the continuous portion of the inner peripheral surface.

19. The endoscope illumination unit according to claim 1, wherein the opposite ends extend in a longitudinal axis direction of the insertion section.

20. An endoscope illumination unit for use on a distal end section of an insertion section of an endoscope, the endoscope illumination unit comprising:

an incident part having two or more incident surfaces onto which illuminating light guided via a light guide from an external light source enters the incident part;

a transparent light guide body including an annular section formed at least partially in a circumferential direction, the annular section having an inner peripheral surface, the light guide body guiding the illuminating light having entered via the incident surface and emitting the illuminating light from an outer surface of the annular section; and two or more scattering materials provided on the inner peripheral surface of the annular section, the two or more scattering materials each being configured to scatter the illuminating light, having entered the light guide body, within the annular section, the two or more scattering materials each being a sheet and each having opposite ends, the opposite ends being applied to continuous cylindrical portions of the inner peripheral surface of the annular section, wherein each sheet is wound in conformity to the inner peripheral surface of the annular section such that each of the opposite ends of one of the sheets is adjacent to a corresponding opposite end of an other of the sheets such that the opposite ends of each of the sheets being positioned at the continuous cylindrical portions of the inner peripheral surface remote from each of the two or more incident surfaces.

\* \* \* \* \*